United States Patent [19]

Abe et al.

[11] 4,321,538

[45] Mar. 23, 1982

[54] NUCLEAR GYROMAGNETIC RESONANCE APPARATUS

[75] Inventors: Katsunobu Abe, Ibaraki; Satoru Kimura, Isunezumi; Norimasa Kamezawa, Ibaraki, all of Japan

[73] Assignee: Hitachi, Ltd., Tokyo, Japan

[21] Appl. No.: 69,057

[22] Filed: Aug. 23, 1979

[30] Foreign Application Priority Data

Aug. 31, 1978 [JP] Japan ................................ 53-107351

[51] Int. Cl.³ .......................................... G01N 27/00
[52] U.S. Cl. .................................................. 324/318
[58] Field of Search ................................ 324/321, 318

[56] References Cited

U.S. PATENT DOCUMENTS

| | | | |
|---|---|---|---|
| 2,960,649 | 11/1960 | Bloch | 324/321 |
| 3,681,683 | 8/1972 | Huber | 324/321 |
| 3,746,971 | 7/1973 | Storeg | 324/321 |

*Primary Examiner*—Michael J. Tokar
*Attorney, Agent, or Firm*—Craig and Antonelli

[57] ABSTRACT

A sample placed in a magnetic field is irradiated with a high frequency wave. The sample is rapidly rotated by a predetermined angle. Throughout the process in which the molecular orientation of the sample returns to the original state subsequently, a nuclear gyromagnetic resonance spectrum obtained from the sample can be observed.

12 Claims, 5 Drawing Figures

NUCLEAR GYROMAGNETIC RESONANCE APPARATUS

BACKGROUND OF THE INVENTION

This invention relates to a nuclear gyromagnetic resonance apparatus and more specifically to a nuclear gyromagnetic resonance apparatus suited for the measurement of viscosity tensor components of a magnetically anisotropic material.

When a liquid crystal, which is a magnetically anisotropic material, is placed in a magnetic field, molecules of the liquid crystal are oriented in a specific direction which is associated with the direction of the magnetic field. If the relation between the orientation of the molecules and the direction of the magnetic field is compulsively changed under this state, the molecules of the liquid crystal are caused to return to the original direction. By observing the nuclear magnetic resonance spectra of the liquid crystal during this return process, it is possible to measure the viscosity tensor components of the liquid crystal from the spectra. Since the viscosity tensor components are one of the most decisive factors for the response time of the liquid crystal display element, observation on the responsibility of the liquid crystal can be obtained from the viscosity tensor components thus measured.

There are known two methods of changing compulsively the relation between the orientation of the liquid crystal placed in the magnetic field and the direction of the magnetic field; one rotating by a certain angle those magnets which are used for generating the magnetic field and the other rotating by a specific angle a probe placed in the magnetic field together with a sample held by the probe while keeping the magnets stationary. The former is disclosed in "Physics Letters", Volume 36A, No. 3, 30 August, 1971, pp 245-246 and the latter is disclosed in "Solid State Communications", Volume 18, No. 11/12, 1976, pp 1591-1593.

The probe generally includes a fluid path of a heat-insulating structure required for measuring a sample at an optional temperature within a wide temperature range, a thermometer and a magnetic field gradient correcting device for compensating for the inhomogeniety of the magnetic field. Hence, it becomes inevitably large in size. In order to obtain a strong magnetic field using magnets as small as possible, on the other hand, it is necessary to minimize the magnet gaps as small as possible. To satisfy these requirements, it is a customary practice in the art to form the cross-section of the probe in a rectangular shape so that its longer sides are in parallel with the edge face of the magnets while its shorter sides are in parallel with the direction of the magnetic field.

If the magnets or the probe is rotated so as to compulsively change the relation between the orientation of the liquid crystal placed in the magnetic field and the direction of the magnetic field, the gaps between the magnets must be made large so that the magnets must be extremely heavy in weight and extremely large in size.

This problem can be solved to a certain extent by removing from the probe means for setting the sample to an optional temperature and the magnetic field gradient correcting device. In this case, however, it is no longer possible to obtain a nuclear gyromagnetic resonance spectrum having high resolution.

SUMMARY OF THE INVENTION

It is therefore an object of the present invention to provide a nuclear gyromagnetic resonance apparatus which is suited for the measurement of viscosity tensor components of a magnetically anisotropic material without enlarging the gaps between magnets.

In accordance with the present invention, there is provided a nuclear gyromagnetic resonance apparatus which comprises means for generating a magnetic field, means for generating a high frequency wave, means for arranging a sample in the magnetic field, a probe including means for feeding the high frequency to the sample and means for detecting nuclear gyromagnetic resonance generated thereby, and means for rotating the sample by a predetermined angle while keeping the probe stationary.

Other objects and features of the present invention will become apparent from the following description taken in conjunction with the accompanying drawings.

DESCRIPTION OF PREFERRED EMBODIMENTS

Figure 1:
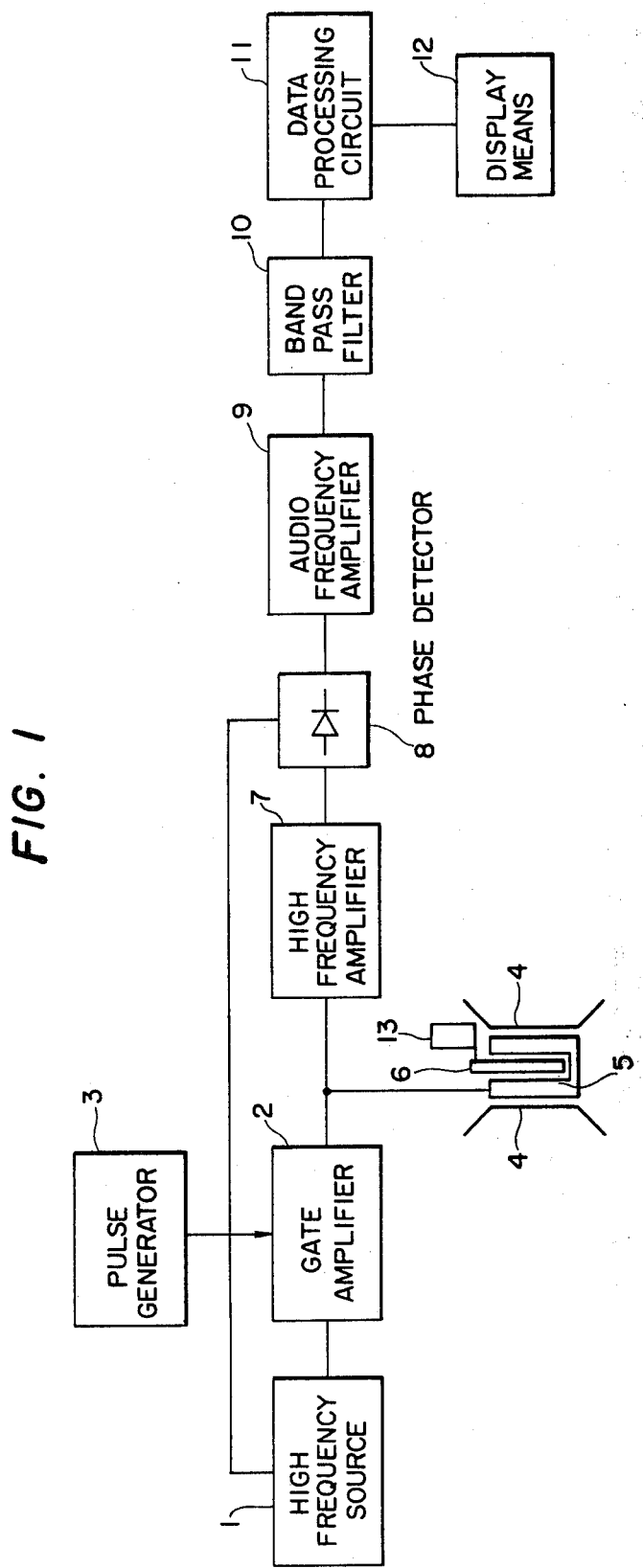
FIG. 1 is a block diagram showing a preferred embodiment of the nuclear gyromagnetic resonance apparatus in accordance with the present invention.

A preferred embodiment of the present invention will now be explained by referring to FIG. 1. A high frequency wave generated from a high frequency source 1 is modulated at a gate amplifier 2 with a pulse generated from a pulse generator 3. A probe 5 is placed in the magnetic field generated by magnets 4 and holds a sample tube 6 filled with a sample. The high frequency wave, which is pulse-modulated, is impressed to the sample inside the sample tube 6 through the probe 5. Accordingly, a free induction decay signal including a simultaneous resonance signal component is detected throughout the OFF-period of the pulse through the probe 5. This signal is amplified by a high frequency amplifier 7 and then subjected to phase detection by a phase detector 8 using the high frequency signal from the high frequency source 1 as a reference signal.

The free induction decay signal consisting of audio frequency components derived from the phase detector 8 is led into a date processing unit 11 through an audio amplifier 9 and a band pass filter 10. The input signal to the data processing unit 11 is subjected to the analog-digital conversion and further to the Fourier transformation, whereby there is obtained a nuclear gyromagnetic resonance spectrum, which is then displayed on display means 12.

To the sample tube 4 is connected a sample-rotating device 13 for rotating the sample inside the sample tube by a certain angle. It is hereby assumed that the sample is a liquid crystal which is a magnetically anisotropic material. This liquid crystal may be a smectic liquid crystal, a nematic liquid crystal or a cholesteric liquid crystal. When this liquid crystal is placed in the magnetic field, the molecules of the liquid crystal are arranged in a specific direction associated with the direction of the magnetic field. When the sample tube 6, and hence the sample therein, is rotated by a predetermined angle by means of the sample-rotating device 13 under this state, the relation between the orientation of the molecules of the liquid crystal and the direction of the magnetic field is compulsively changed, and when rotation of the sample is stopped, the relation between the orientation of the molecules of the liquid crystal and the direction of the magnetic field assumes gradually the original state. Since the nuclear gyromagnetic resonance spectrum can be displayed on the display means 12 throughout this return process, it is possible to measure the viscosity tensor components of the liquid crystal from the spectrum thus displayed.

When rotation of the sample is slow, the relation between the orientation of the molecules of the liquid crystal and the direction of the magnetic field starts returning to the original state even during its rotation. Hence, the faster the rotation of the sample, the more easier does the measurement of the viscosity tensor components become at a higher level of accuracy.

Figure 2:
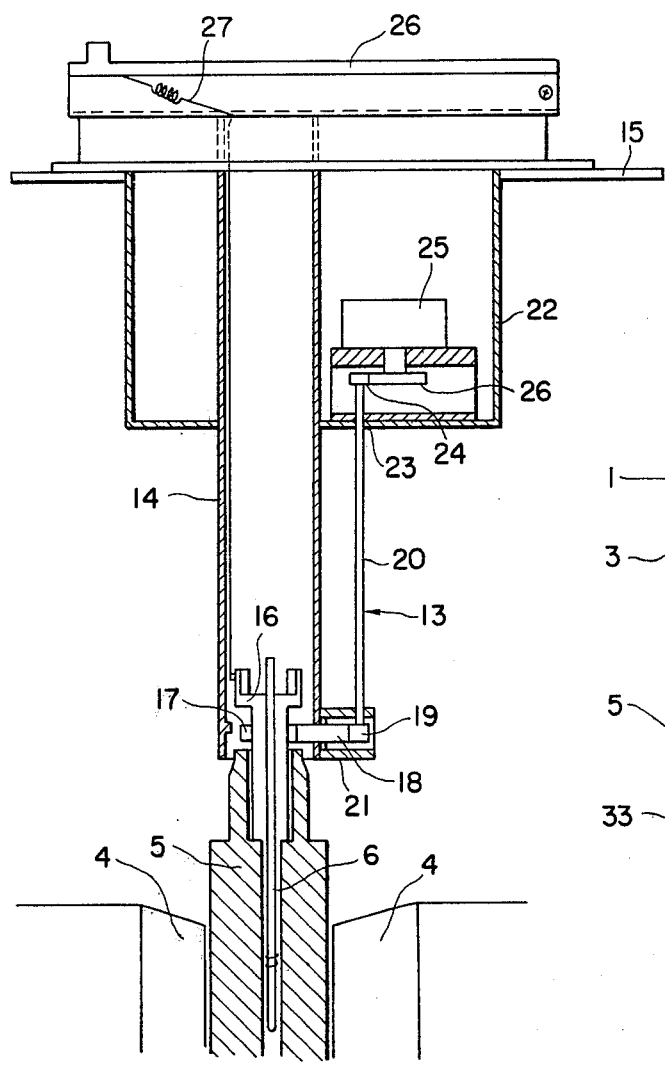
FIG. 2 is a longitudinal sectional view of a preferred embodiment of the mechanical portions of a sample-rotating device for rotating a sample tube held by the probe shown in FIG. 1.

FIG. 2 shows a preferred embodiment of the mechanical portion of the sample-rotating device for rotating the sample tube which is held by the probe shown in FIG. 1. The probe 5, which is placed in the magnetic field formed between the magnets 4, is secured to the lower end of a sample introduction tube 14, and the upper end of this sample introduction tube is secured to the wall 15 of a thermostat chamber for maintaining the magnets 4 at a constant temperature. The probe 5 turnably holds the sample tube 6 via a sample tube holder 16 in such a manner that the sample charged into the tube is placed in the magnetic field. A gear 17 is fitted to the sample tube holder 16 and engages with a gear 19 via another gear 18. The gear 19 is secured to the lower end of a rotary shaft 20, which is in turn supported turnably by a bearing 21 fitted to the sample introduction tube 14 and by a bearing portion 23 of a motor support 22. A gear 24 is secured to the upper end of the rotary shaft 20 and engages with another gear 26 which is directly connected to a pulse motor 25. The pulse motor 25 is supported by the abovementioned motor support 22.

Accordingly, when the gear 26 is rotated by the pulse motor 25, this rotation is transmitted to the sample tube 6 and hence to the sample inside the sample tube, via the gear 24, the rotary shaft 20, the gears 19, 18 and 17 and also via the sample tube holder 16. In this manner, the sample can rapidly be rotated by a predetermined angle.

A lid 26 for opening and closing the upper end of the sample introduction tube 14 is hinged to the wall 15. The lid 26 and the sample tube holder 16 are interconnected to each other by a yarn 27. Accordingly, when opening and closing of the lid 26 are made, the sample tube 6 is allowed to come into and out from the probe 5. In this manner, exchange of the sample can be made easily.

Figure 3:
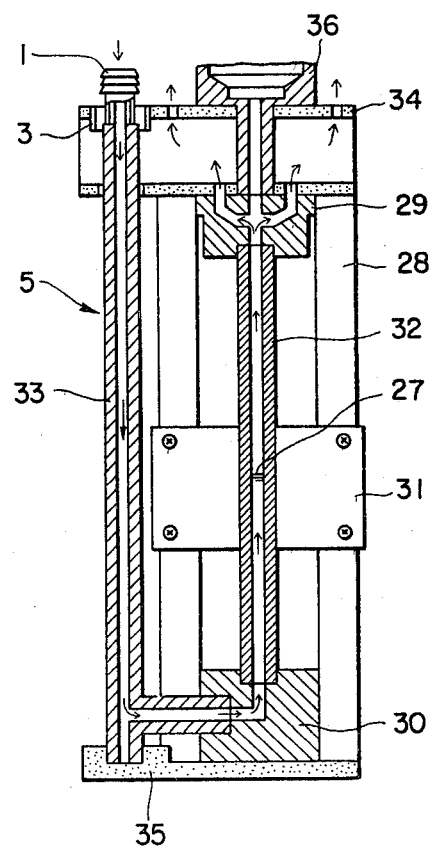
FIG. 3 is a longitudinal sectional side view of a preferred embodiment of the probe shown in FIG. 2.

FIG. 3 is an enlarged longitudinal sectional side view showing a preferred embodiment of the probe 5 shown in FIG. 2. To the body 28 of the probe are secured upper and lower blocks 29, 30 and a magnetic field gradient correcting device 31. A sample tube-insertion tube 32 consisting of a Dewar tube is interposed between the upper block 29 and the lower block 30, and a fluid passage tube 33 consisting of a Dewar tube is connected to the lower block 30 so as to communicate with the sample tube-insertion tube 32. The upper end of the fluid passage tube 33 is supported by a heat non-conductor 34 disposed at the upper end of the probe body 28 while its lower end portion is supported by another heat non-conductor 35 disposed on the lower face of the lower block 30. A sample tube holder-receiver 36 is provided to the heat non-conductor 34 concentrically with the sample tube-insertion tube 32 so as to communicate with the same. A transmission coil 37, which impresses the pulse-modulated harmonic wave to the sample and detects its resonance signal, is provided on the inner face of the sample tube-insertion tube 32. The sample tube 6 (see FIG. 2) is inserted into the sample tube-insertion tube 32 to penetrate through the sample tube holder receiver 36 and through the upper block 29 so that the sample inside the sample tube is placed at the position of the transmission coil 37 and the sample tube holder 16 (see FIG. 2) is seated on the sample tube receiver 36.

In using the apparatus, a fluid consisting of nitrogen gas which is cooled by passing it through liquid nitrogen or of air is caused to flow from the liquid passage tube 33 through the lower block 30 and the sample tube-insertion tube 32 in the route indicated by arrow. The temperature of the fluid is detected by the thermometer (not shown) and on the basis of this temperature detection signal, a heater is turned on and off by means of a temperature controller (not shown), thereby keeping the temperature of the fluid at an optional constant level.

If the sample tube 6 and hence the sample are rotated by a predetermined angle by the sample tube rotating device 13 (see FIGS. 1 and 2) and are stopped at the position of that angle, it is possible to measure the nuclear gyromagnetic resonance during the return process of the relation between the molecular orientation of the liquid crystal as the sample and the direction of the magnetic field that is changed compulsively.

When the nucleus to be measured is a proton, the magnetic field is set to 9,600 Gauses if the high frequency wave is 40 MHz. The cross-section of the probe 5 has a substantially rectangular shape. To reduce the size of the probe as small as possible and to minimize the gap of the magnets to the minimum possible extent, the limit is 16 mm for the shorter side of the probe (the side in parallel to the direction of the magnetic field) and 56 mm for the longer side (the side in parallel to the edge face of the magnet). If the shorter side of the cross-section of the probe 5 is 16 mm, the gap between the magnets can be set to 17 mm. In this case, it is possible to obtain the magnetic field of 9,600 Gauses by setting the weight of the magnets to about 120 kg.

In contrast with the abovementioned arrangement, if the magnet 4 and the probe 5 are rotated instead of the sample tube 6 in order to rotate the sample by a predetermined angle, the magnet gap of at least 60 mm is necessary. Moreover, if the magnet gap is increased from 17 mm to 60 mm, the magnetic field is reduced down to as low as about 8,830 Gauses. For the magnetic field is inversely proportional to the square of the magnet gap. Consequently, even when the magnet gap is increased from 17 mm to 60 mm, the magnet must be enlarged in size and hence, in weight, in order to maintain the necessary magnetic field of 9,600 Gauses. In other words, since the size of the magnet, and hence its weight, are proportional to the magnetic field, the weight of the magnet must be increased to about 230 kg so as to maintain the magnetic field of 9,600 Gauses even if the magnet gap is increased from 17 mm to 60 mm. This means that the weight of the magnet and hence, its size, can be reduced by about a half by rotating the sample instead of rotating the magnet or the probe. This also clarifies how advantageous it is to rotate the sample tube.

According to the abovementioned embodiment, means for maintaining the sample at an optional constant temperature and the magnetic field gradient correcting device are not deleted. Hence, there is no case where the resolving power of the nuclear gyromagnetic resonance measurement is deteriorated.

Figure 4:
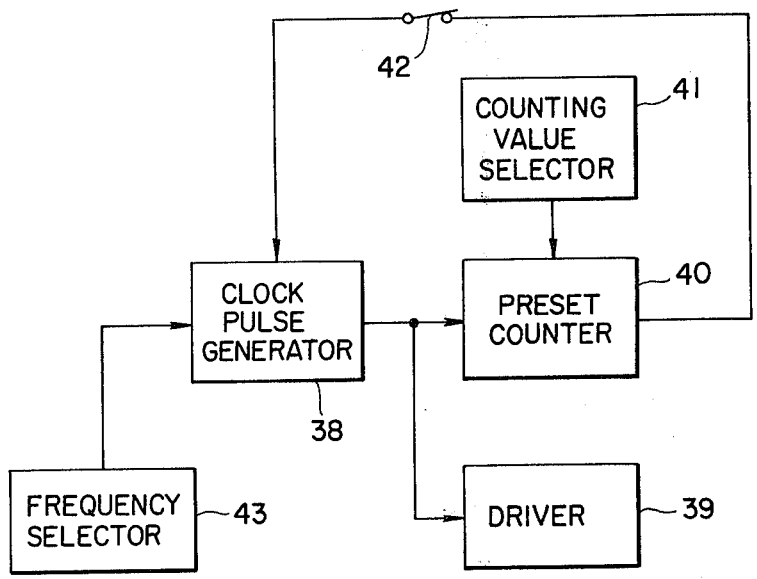
FIG. 4 is a block diagram of a preferred embodiment of the electric portions of a sample-rotating device for rotating the sample tube held by the probe shown in FIG. 1.

FIG. 4 shows a preferred embodiment of the electric circuit of the sample-rotating device for rotating the sample which is held by the probe shown in FIG. 1. The output pulse of a frequency-variable clock pulse generator 38 is applied to the pulse motor 25 (see FIG. 2) through a driver 39 whereby the pulse motor starts rotating. The clock pulse from the clock pulse generator 38 is also applied to a preset counter 40. This counter counts the number of the clock pulses applied thereto and applies a reset pulse to the clock pulse generator 38 via a switch 42 when the number of the clock pulses counted reaches a count valve which is pre-determined by a variable counter-setter 41. The reset pulse stops the feed of the clock pulses from the clock pulse generator 38 to the driver 39. Accordingly, the pulse motor 25 (see FIG. 2) and hence, the sample, are allowed to rotated by an angle corresponding to the count value set by the variable setter-counter 41, and the angle of rotation can be optionally selected by changing the count value to be set by the variable counter-setter 41. Further, the speed of revolution of the sample can be changed either by changing the pulse frequency of the clock pulse generator 38 by means of a pulse frequency setter 43 or by changing optionally the number of teeth of the gears 17, 18, 19, 24 and 26.

Incidentally, when the switch 41 is opened, the sample keeps rotating continuously. As is well known, this can be used for making the magnetic field gradient average and thus improving the resolving power.

Figure 5:
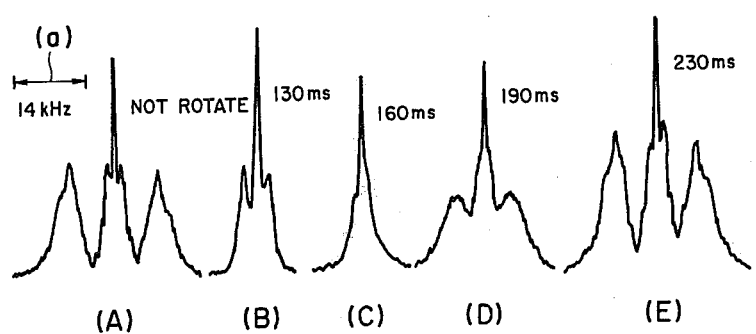
FIG. 5 is a chart showing the nuclear gyromagnetic resonance spectrum measured by an embodiment of the nuclear gyromagnetic resonance apparatus in accordance with the present invention.

FIG. 5 illustrates the nuclear gyromagnetic resonance spectrum of the proton measured by the inventor of the present invention in accordance with the method of Fourier transform gyromagnetic resonance spectrometry of a Nematic Phase 5 (NP-5) produced by E. Merck Co. as the sample. In this chart, symbol (A) represents the data when no rotation is imparted to the sample while symbols (B) through (E) represent the data obtained at 130 milli-second, 160 milli-second, 190 milli-second and 230 milli-second after rotating the sample by 90 degrees, respectively. It can be appreciated from these data that the molecular orientation of the sample returns substantially to the original state after about 230 milli-second. In FIG. 4, the axis of abscissa represents the frequency while the axis of the ordinate does a quantity associated with resonance absorption. Symbol (a) represents a reference scale of the abscissa of 14 KHz which is common to all the data. The conditions of the measurement are as follows;

| | |
|---|---|
| frequency of the high frequency wave | 40 MHz |
| magnetic field | 6,900 Gauses |
| sample temperature | 35° C. |

The number of pulses given to the pulse motor 25 for rotating the sample by 90 degrees is 90 and the time required for it is 50 milli-second.

As can be seen from the data of FIG. 4, too, the return of the molecular orientation of the magnetically anisotropic material is effected within an extremely short period so that rotation of the sample by a predetermined angle must also be made extremely rapidly. Though the abovementioned embodiment uses the pulse motor as the drive source suitable for such purpose, a servo-motor, a rotary solenoid or a latching relay may also be used as a drive source which rotates the sample extremely rapidly.

Since the return of the molecular orientation of a magnetically anisotropic material is effected within an extremely short period of time, the nuclear gyromagnetic resonance spectrum of such a material must be obtained instantaneously. From this aspect, it is preferred to use a Fourier transformation type nuclear gyromagnetic resonance apparatus in the embodiment of the invention such as described above rather than a continuous wave type gyromagnetic resonance apparatus wherein a continuous high frequency is applied to the sample disposed in the magnetic field and either the high frequency or the magnet is swept in order to obtain the nuclear gyromagnetic resonance spectrum.

The magnet and the probe are extremely heavier than the sample and consequently, it is desired to rotate the sample rather than the magnet and the probe. For this method provides quicker rotation and more accurate stop of rotation. This is another advantage of the method of rotating the sample in comparison with the method of rotating the magnet and the probe.

Since various changes and modifications in detail of the aforementioned preferred embodiments of the present invention would be obvious to those skilled in the art, the scope of the invention should be decided in view of the appended claims.

What is claimed is:
1. A nuclear gyromagnetic resonance apparatus comprising:
 means for generating a magnetic field; means for generating a high frequency wave; means for placing a sample in said magnetic field; a probe including means for feeding said high frequency wave to said sample and for detecting nuclear gyromagnetic resonance generated thereby; and means for rotating said sample by a predetermined angle while keeping said probe stationary, said means for rotating said sample including means for variably setting said predetermined angle.
2. The nuclear gyromagnetic resonance apparatus as defined in claim 1 wherein said means for rotating said sample further includes a pulse motor, means for generating pulses for rotating said pulse motor and means for counting the number of said pulses for stopping revolution of said pulse motor when the number of said pulses counted reaches a predetermined value, and said means for variably setting said predetermined angle comprises means for variably setting said predetermined value.
3. A nuclear gyromagnetic resonance apparatus comprising:

means for generating a magnetic field; means for generating a high frequency wave; means for placing a sample in said magnetic field; a probe including means for feeding said high frequency wave to said sample and for detecting nuclear gyromagnetic resonance generated thereby; and means for rotating said sample by a predetermined angle while keeping said probe stationary, said means for rotating said sample including a pulse motor, means for generating pulses for rotating said pulse motor and means for counting the number of said pulses and for stopping revolution of said pulse motor when the number of said pulses counted reaches a predetermined value, said means for stopping revolution of said pulse motor being equipped with means for varying said predetermined value.

4. A nuclear gyromagnetic resonance apparatus comprising:

means for generating a magnetic field; means for generating a high frequency wave; means for placing a sample in said magnetic field; a probe including means for feeding said high frequency wave to said sample and for detecting nuclear gyromagnetic resonance generated thereby; and means for rotating said sample by a predetermined angle while keeping said probe stationary, said means for rotating said sample including a pulse motor, means for generating pulses for rotating said pulse motor and means for counting the number of said pulses and for stopping revolution of said pulse motor when the number of said pulses counted reaches a predetermined value, and means for generating said pulses being equipped with means for varying the frequency of said pulses.

5. A nuclear gyromagnetic resonance apparatus comprising:

means for generating a magnetic field; means for generating a high frequency wave; means for pulse-modulating said high frequency wave; means for placing a sample in said magnetic field; a probe including means for feeding said pulse-modulated high frequency wave to said sample and for detecting a free induction decay signal generated thereby; means for converting said free induction decay signal into a nuclear gyromagnetic resonance spectrum signal; and means for rotating said sample by a predetermined angle while keeping said probe stationary, said means for rotating said sample including means for variably setting said predetermined angle.

6. The nuclear gyromagnetic resonance apparatus as defined in claim 5 wherein said means for rotating said sample is equipped with a pulse motor and means for rotating said pulse motor by a predetermined quantity, and said means for variably setting said predetermined angle comprises means for variably setting said predetermined quantity.

7. A nuclear gyromagnetic resonance apparatus comprising:

means for generating a magnetic field; means for generating a high frequency wave; means for pulse-modulating said high frequency wave; means for placing a sample in said magnetic field; a probe including means for feeding said pulse-modulated high frequency wave to said sample and for detecting a free induction decay signal generated thereby; means for converting said free induction decay signal into a nuclear gyromagnetic resonance spectrum signal; and means for rotating said sample by a predetermined angle while keeping said probe stationary, said means for rotating said sample being equipped with a pulse motor and means for rotating said pulse motor by a predetermined quantity, said means for rotating said pulse motor including means for generating pulses for rotating said pulse motor and means for counting the number of said pulses and for stopping rotation of said pulse motor when the number of said pulses counted reaches a predetermined value.

8. The nuclear gyromagnetic resonance apparatus as defined in claim 7 wherein said means for stopping said pulse motor include means for selectively stopping the operation of said stop means.

9. The nuclear gyromagnetic resonance apparatus as defined in claim 7 wherein said means for stopping said pulse motor include means for changing said predetermined value and means for varying the frequency of said pulses.

10. The nuclear gyromagnetic resonance apparatus as defined in claim 7 wherein said means for stopping said pulse motor include means for stopping selectively the operation of said stop means, means for changing said predetermined value and means for varying the frequency of said pulses.

11. The nuclear gyromagnetic resonance apparatus as defined in claim 1, wherein said means for rotating said sample enables stopping of said sample at the position of said predetermined angle.

12. The nuclear gyromagnetic resonance apparatus as defined in claim 5, wherein said means for rotating said sample enables stopping of said sample at the position of said predetermined angle.

* * * * *